United States Patent [19]

Cewers

[11] Patent Number: 5,694,924
[45] Date of Patent: Dec. 9, 1997

[54] ANESTHETIC ADMINISTRATION SYSTEM WITH ACTIVE REGULATION OF THE VOLUME OF THE GAS RESERVOIR DURING A BREATHING CYCLE

[75] Inventor: Göran Cewers, Lund, Sweden

[73] Assignee: Siemens-Elema AB, Solna, Sweden

[21] Appl. No.: 728,862

[22] Filed: Oct. 10, 1996

[30] Foreign Application Priority Data

Oct. 19, 1995 [SE] Sweden .................. 9503665

[51] Int. Cl.$^6$ .......................... A62M 7/00; A61M 16/00
[52] U.S. Cl. .................. 128/204.21; 128/204.29; 128/205.12; 128/205.13; 128/205.15
[58] Field of Search .................. 128/204.18, 204.21, 128/204.26, 204.28, 205.15, 205.16, 205.24

[56] References Cited

U.S. PATENT DOCUMENTS

| | | |
|---|---|---|
| 4,637,385 | 1/1987 | Rusz . |
| 4,883,051 | 11/1989 | Westenskow et al. ............. 128/204.21 |
| 4,928,683 | 5/1990 | Westerkamp et al. . |
| 5,107,830 | 4/1992 | Younes ........................ 128/204.21 |
| 5,471,979 | 12/1995 | Psaros et al. . |
| 5,520,172 | 5/1996 | Obermayer .................. 128/204.21 |

FOREIGN PATENT DOCUMENTS

| | | |
|---|---|---|
| 0 621 049 | 10/1994 | European Pat. Off. . |
| 2 062 475 | 5/1981 | United Kingdom . |
| WO 88/07876 | 10/1988 | WIPO . |

*Primary Examiner*—V. Millin
*Assistant Examiner*—Robert N. Wieland
*Attorney, Agent, or Firm*—Hill, Steadman & Simpson

[57] ABSTRACT

An anesthetic system, primarily intended for a closed breathing circuit, has an inspiratory line, an expiratory line and a connecting line which form a closed gas line system with the inspiratory line and the expiratory line. A first check valve and a second check valve are arranged in the connecting line to control the direction of gas flow in the gas line system. A first gas reservoir and a second gas reservoir are also connected to the connecting line. The gas reservoirs are functionally interconnected so an increase in the volume of one results in a corresponding reduction in the volume of the other, and vice-versa. The changes in volume are actively controlled by a control system. During inspiration, respiratory gas is carried to the patient from a hand ventilator at the same time as respiratory gas is carried from the first gas reservoir to the second gas reservoir. During expiration, respiratory gas is carried from the patient to the first gas reservoir, and respiratory gas from the second gas reservoir is carried to the hand ventilator with a flow of fresh gas from a source of fresh gas. All flows are regulated to make them identical.

14 Claims, 4 Drawing Sheets

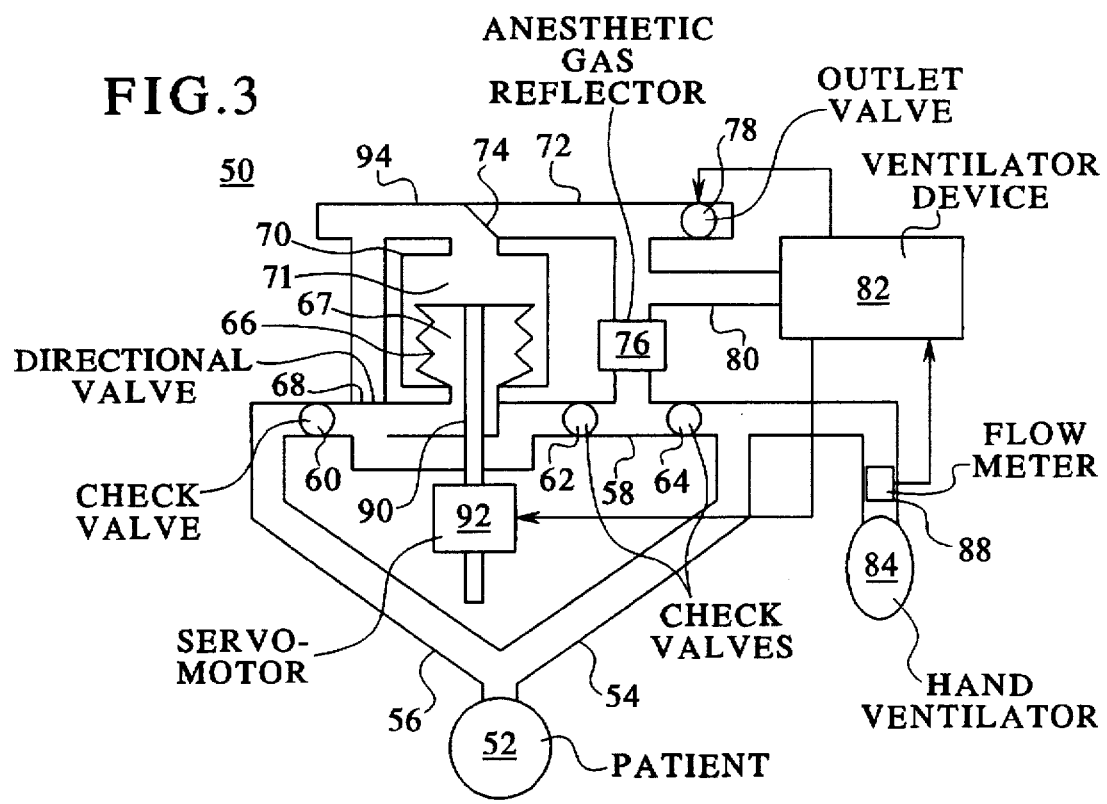
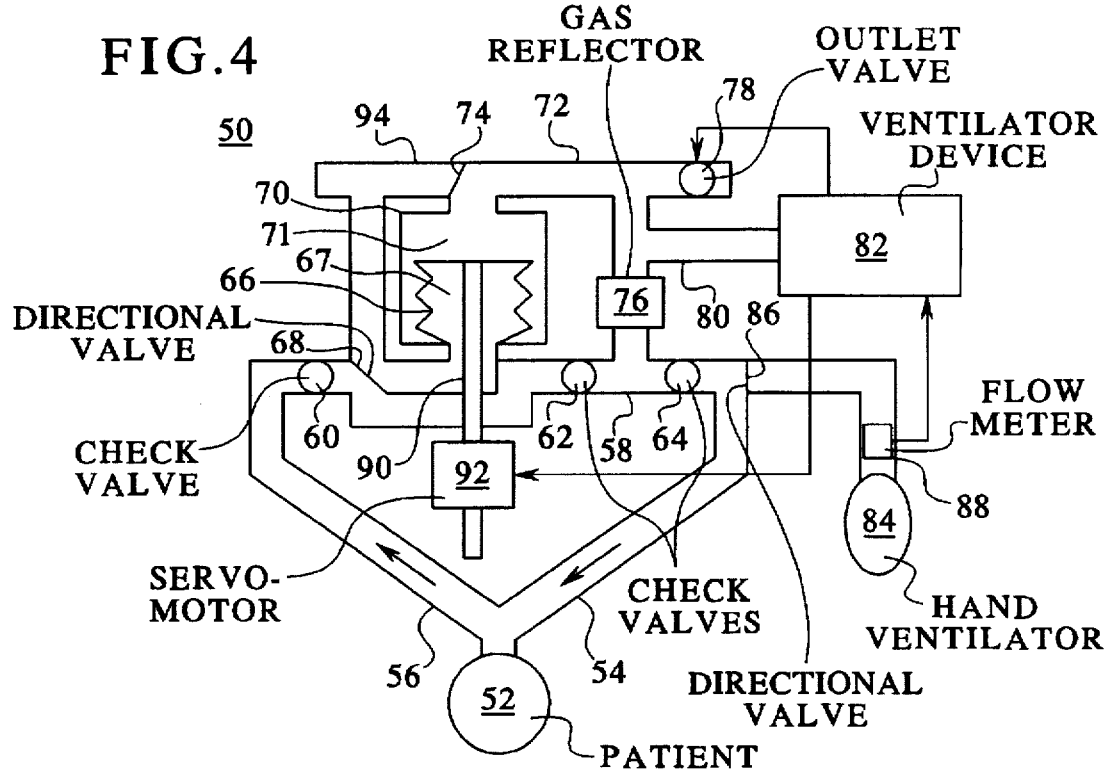

ANESTHETIC ADMINISTRATION SYSTEM WITH ACTIVE REGULATION OF THE VOLUME OF THE GAS RESERVOIR DURING A BREATHING CYCLE

BACKGROUND OF THE INVENTION

1. Field of the Invention

The present invention is directed to an anesthetic system of the type having an inspiration line and an expiration line connectable to a patient and a gas reservoir with a variable volume which, during a respiration cycle, is alternately filled and emptied of respiratory gas for administering the respiratory gas to the patient.

2. Description of the Prior Art

British Specification 2 062 475 describes an anesthetic system having an inspiratory line for carrying respiratory gas to the patient and an expiratory line for carrying respiratory gas away from the patient. A bellows capable of increasing or decreasing its volume, depending on whether inspiration or expiration is involved, is connected to these lines. During inspiration, the bellows is pneumatically compressed, so respiratory gas flows out of the bellows, through the inspiratory line to the patient. A first check valve is located in the inspiratory line near the patient, and a second check valve is located in the expiratory line. The check valves control the direction of respiratory gas flow, so it does not flow in the wrong direction. In expiration, the pneumatic pressure is disconnected and the bellows is allowed to expand, whereupon respiratory gas flows from the patient, through the expiratory line, back to the bellows.

Since the same respiratory gas is re-used a number of times in this known anesthetic system, a carbon dioxide absorber is arranged in the inspiratory line to remove carbon dioxide from respiratory gas during the inspiratory phase. A source of fresh gas is also connected to the inspiratory line. This supplies fresh respiratory gas to the line system (the inspiratory and expiratory lines) to replace respiratory gas which has been absorbed by the patient, absorbed by the carbon dioxide absorber or leaked out of the system. In general, a continuous flow of fresh respiratory gas is supplied with the same composition desired for respiratory gas in the line system. In other words, the gases consumed and the extent to which they are consumed are not taken into account. This is because of the difficulty in accurately and simply determining the uptake of oxygen, nitrous oxide and anesthetic gas in the patient, and carbon dioxide in the carbon dioxide absorber and leakage. (Leakage is especially hard to determine, since different gases have different tendencies to leak out of the system. This is partly due to the prevailing partial pressures of the gas components on the input and output sides of the system, respectively. In extreme instances, gas can also leak into the system from the outside, especially $N_2$ which has a high partial pressure in the atmosphere.)

The operating mode of this known anesthetic system is often referred to as a "closed system", because of its re-use of respiratory gas. Since anesthetic gases are generally very expensive, an anesthetic system having a low consumption of anesthetic gas is economically far more advantageous than "open systems", in which no respiratory gas is re-used, or "semi-closed systems" which re-use a large or small part of the respiratory gas.

Known so-called closed anesthetic systems, however, are not completely closed, in the literal sense. As already noted, fresh respiratory gas is supplied to the above known anesthetic system in a continuous flow. At the same time, a relatively low positive pressure is sought in the line system, since the patient usually has healthy lungs with high compliance. Accordingly a pop-off valve is connected to the expiratory line to open and bleed off surplus gas from the line system, even at relatively low positive pressures in the line system. Since the supply of fresh respiratory gas usually exceeds the system's consumption of gas, respiratory gas is released through the pop-off valve in every respiratory cycle. As a result, there is a loss of gas which is not inconsiderable.

Another disadvantage of this type of anesthetic system is that the check valves and carbon dioxide absorber constitute impediments in the flow paths, therefore posing major resistance to the patient's expiration. (Some systems also include a humidifier especially open and semi-closed anesthetic systems whose gas consumption is already high from the beginning.) When the patient breathes spontaneously, these components also serve as inspiratory impediments for the patient, impediments which must be overcome every time the patient inhales. Another problem caused by these components is the fact that the distance from the patient to the equipment increases. This means that longer lines are needed for connecting the anaesthesia system to the patient. This contributes to increased resistance and an increase in the line system's compressible volume. In sum, these problems result in a poor response time for the system.

The above known anaesthesia system can also be switched to a mode for manual ventilation of the patient by means of a hand ventilator. The same problems present in the mechanical ventilation mode are present in the manual ventilation mode. In manual ventilation, the physician wants to feel the response of the patient's lungs through the hand ventilator, which usually consists of a soft, bellows-like bag. This is naturally harder to achieve because of all the components between the patient and the bag.

Both mechanical and manual ventilation of the patients occur in open, semi-closed and closed anaesthesia systems. The physician often wishes to switch between different modes, depending on the situation (the type of patient, the time in the treatment etc.). In systems devised to permit simple switching from e.g. a closed mechanical operating mode to an open manual operating mode, all the components, such as check valves, are still retained, and the problems noted above for a closed system also apply, in general, to other operating modes.

Another problem which has occurred in conjunction with the introduction of newer anesthetics, sevoflurane in particular, is that they cannot be used with normal carbon dioxide absorbers. This is because soda lime is usually employed to absorb carbon dioxide, and the anesthetic (sevoflurane) is decomposed by soda lime.

Most of the above problems and disadvantages encountered in manual ventilation with fully open systems are completely avoided with the ventilation system described in Swedish Published Application 470 417 corresponding to European Application 0 621 049. In this known ventilator system, a flow meter is arranged near the hand ventilator. During inspiration, gas is fed to the patient by manually squeezing the hand ventilator bellows. Since the system is open, there is no need for check valves, so the physician always maintains complete control over the response of the lungs to bellows compression throughout inspiration. In expiration, an advanced control method is employed in which fresh gas is fed into the hand ventilation bellows at a rate equivalent to the patient's expired gas flow and gas expired by the patient is evacuated from the system. This enables the physician to feel the response of and behavior of the lungs even during expiration, even though the patient is not actually expiring into the hand ventilator. Control can also be based on measurements of pressure or flow, closer to the patient.

The described open ventilator system is suitable for all forms of manual patient ventilation and can also be used with e.g. sevoflurane, which must still be used in open systems, although with a relatively heavy consumption of sevoflurane. This known ventilator system, however, is not adapted to nor devised for a closed system, which is the type of system most often used for narcosis.

SUMMARY OF THE INVENTION

An object of the present invention is to provide an anesthetic system of the above type which addresses the problems posed by known closed anesthetic 5 systems and which can be used, in a simple manner, even for other operating modes.

The above object is achieved in accordance with the principles of the present invention in an anesthetic administration system having an inspiration line and a respiratory line connectable to a patient, a gas reservoir with a variable volume which, during a respiration cycle of the patient, is alternately filled and emptied of respiratory gas, and control means, connected to the gas reservoir, for actively regulating the volume of the gas reservoir relative to a reference value throughout the patient's entire breathing cycle.

The basic concept of the invention can, in principle, be described as follows. The volume of the gas reservoir is actively controlled throughout the entire breathing cycle. This control is based on a reference value which shall be the target. The reference value can be a variable or a measurement value in some other part of the line system. In principle, the patient only needs to overcome the minimal resistance posed by the gas lines themselves. Moreover, these lines can be made much shorter than in the known systems, since they do not need to incorporate any components.

In one embodiment of the inventive anesthetic system, the system is in the form of a triangle in which the inspiratory and expiratory lines, which do not contain any components, constitute two sides of the triangle and a connecting line between the inspiratory line and the expiratory line serves as the third side. The gas reservoir and other components installed to refine the system's operation, such as check valves, are located in the connecting line. Since the gas reservoir is connected to a control device which actively regulates the variable volume in both inspiration and expiration, the control device overcomes the flow resistance posed by check valves and other components.

In another embodiment of the anesthetic system according to the invention, a carbon dioxide absorber is arranged in the connecting line. The delivery of fresh respiratory gas is simultaneously controlled, so it is minimal, only corresponding to the actual consumption of gas by the patient and in the carbon dioxide absorber. This is feasible because of the control device's exact control of the gas reservoir's variations in volume.

In a third embodiment of the anesthetic system according to the invention, an anesthetic gas reflector is arranged in the connecting line. In principle, the anesthetic gas reflector is a filter, which extracts anesthetic gas from respiratory gas when the latter passes in one flow direction. When new respiratory gas (with or without a considerably lower concentration of anesthetic gas) is supplied from the other direction, the anesthetic gas extracted by the filter is released into the new respiratory gas. In other words, only the anesthetic gas in the respiratory gas is re-used and no other gases. The anesthetic gas reflector and its function are described in detail in PCT Application WO 88/07876 and European Application 455 049.

As an, alternative to check valves to inure flow in the proper direction, a fan can be arranged in the line system to force gas to flow in only one direction. one example of this use is described in European Application 281 180.

DESCRIPTION OF THE DRAWINGS

FIG. 3 is a schematic illustration of a second embodiment of the anesthetic system, according to the invention, in a first operating mode.

FIG. 4 shows the second embodiment of FIG. 3 in a second operating mode.

DESCRIPTION OF THE PREFERRED EMBODIMENTS

Figure 1:
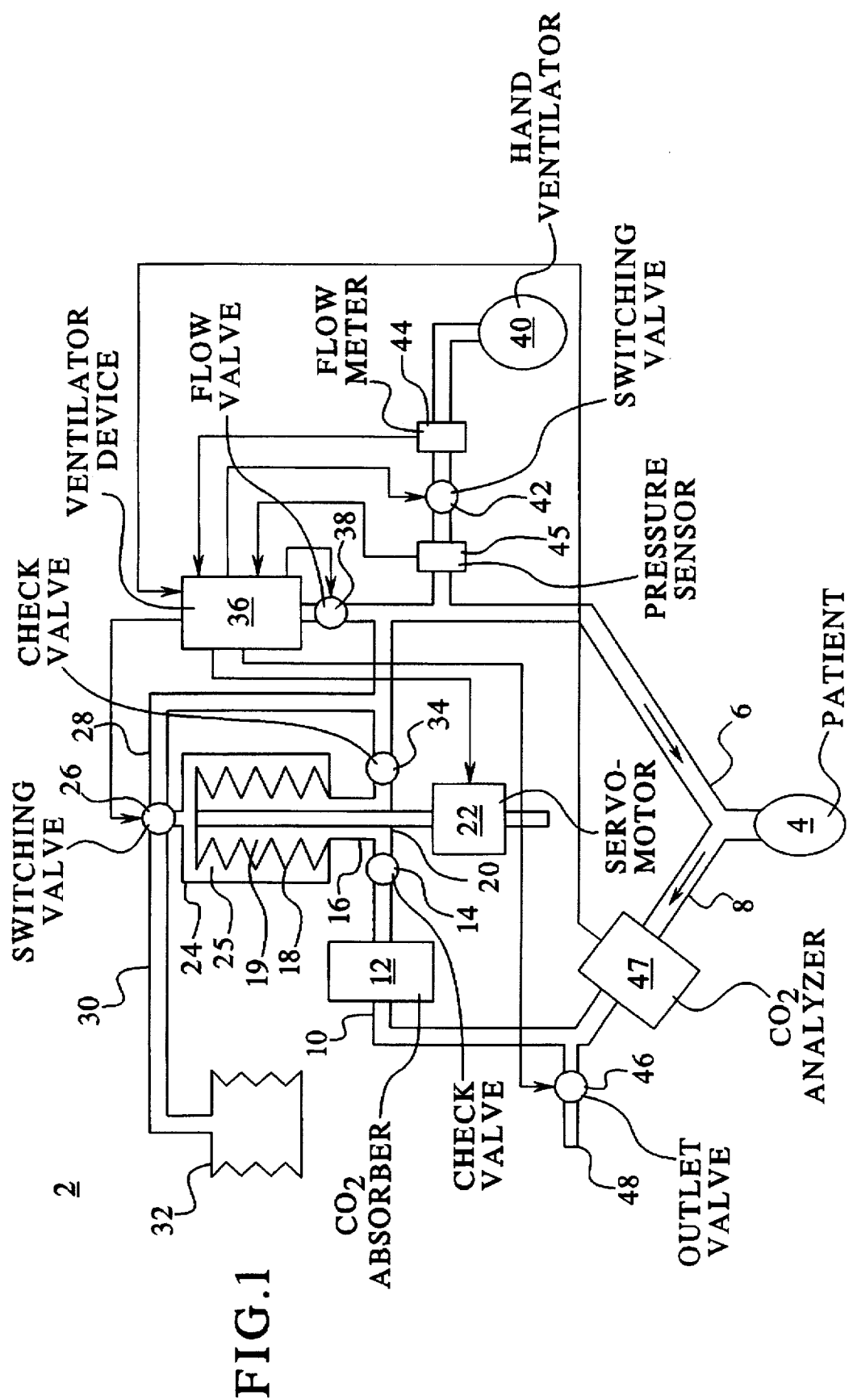
FIG. 1 is a schematic illustration of a first embodiment of the anesthetic system according to the invention at a first point in time in a breathing cycle.
Figure 2:
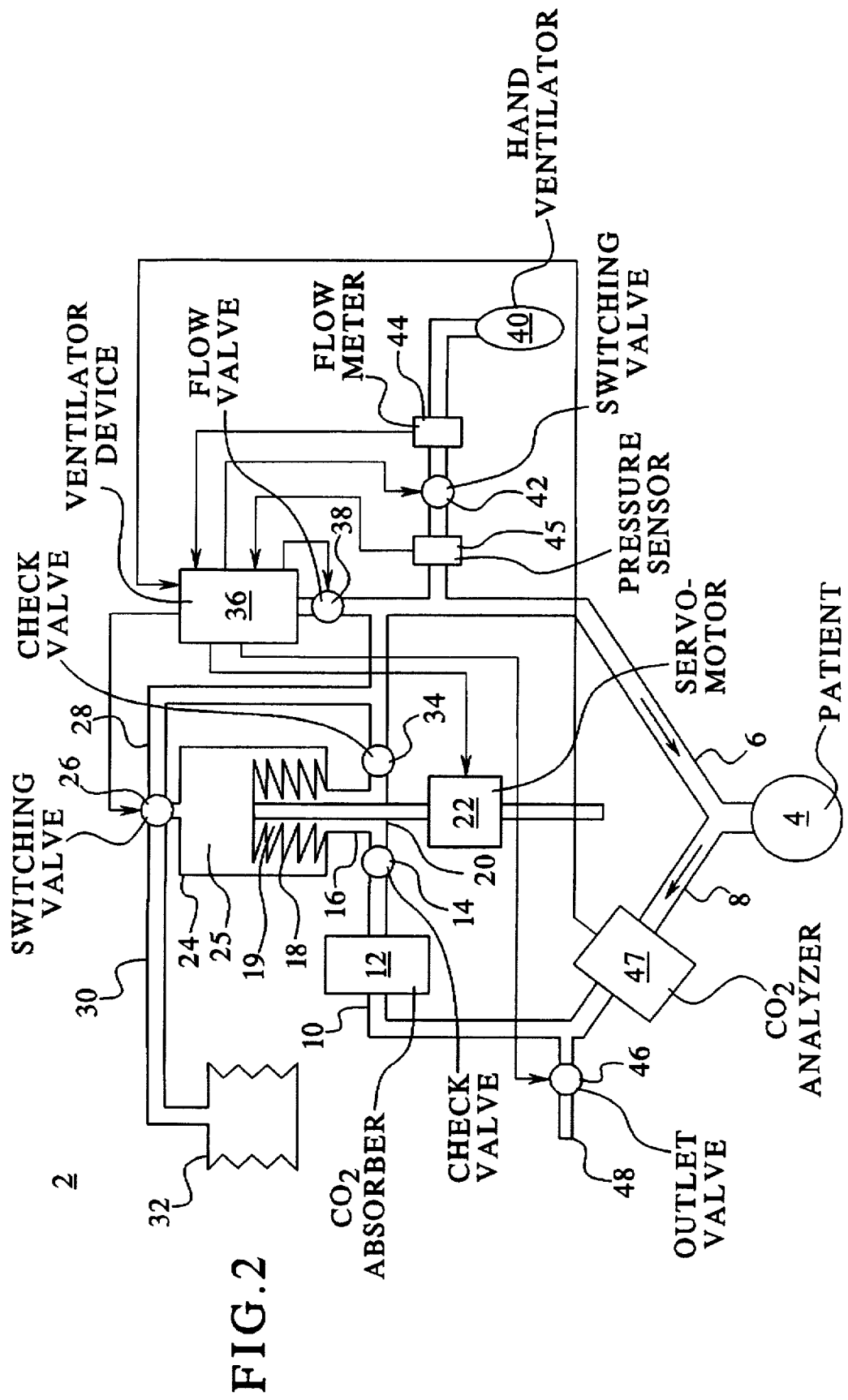
FIG. 2 shows the first embodiment of FIG. 1 at a second point in time in the breathing cycle.

A first embodiment of the anesthetic system according to the invention is described in FIGS. 1 and 2 and is generally designated 2. The anesthetic system 2 is connected to a patient 4 and has a respiratory gas circulation system including an inspiratory line 6, an expiratory line 8 and a connecting line 10. A carbon dioxide absorber 12 and a first check valve 14 are arranged in the connecting line 10. The first check valve 14 is arranged so that only respiratory gas from the expiratory line 8 is able to pass. The connecting line 10 is also connected, via a gas connector 16, to the interior of a bellows 18. The interior space serves as a first gas reservoir 19. The bellows 18 is mechanically connected to a control rod 20 operated by a servo-motor 22. The volume of the bellows 18 (the volume of the first gas reservoir 19) can be regulated very rapidly and accurately. The bellows 18 is enclosed in a rigid container 24, so the space between the bellows 18 and the outer wall of the container 24 forms a second gas reservoir 25. The second gas reservoir 25 can be connected to the connecting line 10 via a first switching valve 26 and a connection line 28. The first switching valve 26 can also be set so that the second gas reservoir is connected to a drive gas bellows 32 via a drive gas line 30.

A second check valve 34 is arranged between the gas connector 16 and the connection line 28, so that respiratory gas is only able to flow toward the inspiratory line 6. A ventilator device 36 is also connected to the connecting line 10, downstream from the second check valve 34. The ventilator device 36 also includes, inter alia, a fresh gas source containing fresh respiratory gas and a control unit which controls and monitors all functions in the anesthetic system 2. The flow of fresh respiratory gas can be regulated with 10 great accuracy via a flow valve 38.

A hand ventilator 40 can also be connected to the connecting line 10 or to the inspiratory line 6. The hand ventilator 40 can be selectively connected to or disconnected from the anesthetic system 2 via a second switching valve 42. When the hand ventilator 40 is connected, the respiratory gas flow is measured in a flow meter 44.

Finally, an outlet valve 46 is arranged in an evacuation line 48 in the anesthetic system 2. Gas can be quickly evacuated from the line system via the outlet valve 46, e.g. in conjunction with waking up the patient 4 from the narcosis. The outlet valve 46 can also be devised for other functions, which are described below. The evacuation line 48 can be connected to some form of fixed or mobile gas evacuation system found in hospitals.

The anesthetic system 2 can operate according to a number of different respiratory system principles, including open, semi-closed and closed. The anesthetic system 2 can also be optionally operated manually or mechanically. The anesthetic system 2, set up as a closed system, will be described in the following. FIG. I shows the closed system at the onset of an inspiration, and FIG. 2 shows the system at the onset of an expiration.

The closed system will first be described for manual ventilation of a patient, i.e. when a physician supplies the patient 4 with respiratory gas by squeezing a hand ventilator 40. In this operating mode, the first switching valve 26 is set so that the second gas reservoir 25 is connected to the connecting line 10 via the connection line 28, and the second switching valve 42 is set so that the connection between the hand ventilator 40 and the connecting line 10 is open and the outlet valve 46 is closed.

When the physician squeezes the hand ventilator 40, respiratory gas flows out of the bag, through the inspiratory line 6 and on to the patient 4. At the same time, the servo-motor 22 controls the control rod 20 so that the bellows 18 is compressed to a degree directly related to the flow value measured by the flow meter 44. Control is exercised so the volume of the first gas reservoir 19 decreases to the same extent as the volume of the hand ventilator 40 decreases when respiratory gas is supplied to the patient 4, i.e., with the same flow. Gas in the first gas reservoir 19 then flows into the connecting line 10 and passes the second check valve 34, subsequently flowing up through the connection line 28, past the first switching valve 26 and down into the second gas reservoir 25. The flow of respiratory gas from the first gas reservoir 19 to the second gas reservoir 25 takes place without in any way affecting gas flowing from the hand ventilator 40 to the patient 4. The same amount of gas flows from the interior (the first gas reservoir 19) of the bellows 18 as flows to its outlet side (the second gas reservoir 25), i.e. the bellows 18 can be regarded as a short-circuited loop for bellows flow, and no gas flows out of or into this loop.

At the end of inspiration, a volume of respiratory gas, corresponding to the tidal volume supplied to the patient 4, has accordingly been transferred from the first gas reservoir 19 to the second gas reservoir 25.

When expiration commences, i.e., when the physician releases the hand ventilator 40 (slowly or rapidly), respiratory gas will flow from the patient 4, through the expiratory line 8 and connecting line 10 to the bellows 18. In this route, the respiratory gas passes the carbon dioxide absorber 12. The flow passing the hand ventilator 40 can be regarded as a flow for controlling the expiration of the patient 4. This control flow controls the position of the bellows 18 by means of the control rod 20 and servo-motor 22 so that the volume of the first gas reservoir 19 increases at the same rate as respiratory gas flows out of the patient 4. This control can be exercised in any of the ways described in the cited document Swedish Published Application 470 417. When the change in the volume of the bellows 18 is actively controlled in this manner, the flow resistance posed by the carbon dioxide absorber 12 and the first check valve 14 will be overcome by the action of the bellows 18. For the patient 4, this means that he or she can exhale virtually without encountering any resistance in the line system, and it is only the physician's decreasing pressure on the hand ventilator 40 that is capable of impeding the expiration of the patient 4.

At the same time, respiratory gas from the second gas reservoir 25 is sent, via the connection line 28 and the connecting line 10, to the hand ventilator 40. Since hand ventilator flow is the guiding flow for the bellows 18, flow into—the absorber 12 must be somewhat greater than flow leaving the absorber 12 because of the absorption of carbon dioxide. This reduces the amount of gas in the system. In conjunction with this transfer of respiratory gas, however, a small amount of fresh respiratory gas is added, via the flow valve 38 and the ventilator device 36. This small amount of fresh respiratory gas compensates for the volume of gas absorbed in the carbon dioxide absorber 12. During the expiratory phase, the physician is in a good position to feel the breathing efforts of patient 4 and can therefore more easily assess the depth of anesthesia of the patient 4.

The additional fresh respiratory gas is fed directly to the hand ventilator 40, in which it is mixed with re-used respiratory gas from the gas reservoir 25, and most of it ends up in the hand ventilator 40. The additional volume of gas supplied as fresh gas flows on in the form of a bypass flow, via the inspiratory line 6, the expiratory line 8 and on into the absorber 12. The amount of fresh gas needed to sustain the system's gas volume can be controlled by dispensing fresh gas so that a given pressure is maintained in the system. one aid for controlling the flow of fresh gas can be obtained by monitoring expiratory flow plus an estimated $CO_2$ concentration in expired air, or by measuring the $CO_2$ production of the patient 4. This control can utilize the flow signal from the flow meter 44, a pressure signal from a pressure sensor 45 arranged in the system and a measurement signal from a $CO_2$ analyzer 47 which can be connected to the expiratory line 8. Additional pressure and flow sensors can be arranged as redundant sensors for safety or for monitoring. only the fresh gas required to compensate for consumption in the system will accordingly be supplied.

Concentrations of the other relevant gas components can be measured during inspiration and expiration in measurement devices (not shown in the figure) for that purpose, and consumption of the respective gas can be calculated from the difference in gas concentration between inspiration and expiration. This can also be utilized for determining the composition of the fresh respiratory gas which is to be supplied, however, a number of fast gas meters is needed for this procedure to work properly. No such array of meters is necessary for the anesthetic system 2 to operate. In the same way set forth in Swedish Published Application 470 417, the physician will not be able to feel any difference compared to the situation in which the patient 4 expires straight into the hand ventilator 40.

The anesthetic can be supplied in virtually every known manner, both as a gas and a liquid, with fresh gas or separately. Any measurement of the anesthetic's concentration can be performed at any desired point in the system.

Since the entire flow cycle in the anesthetic system 2 is regulated by a servo-system with extreme accuracy, system pressure can be kept on a constantly low level, thus no gas needs to be released from the system. The outlet valve 46 can therefore be completely closed in this operating mode. In other words, a practically closed system is achieved. The anesthetic system 2 is also very compact and can be located close to the patient 4, providing advantages for the physician monitoring the patient 4. The patient 4 will easily be able to breath spontaneously whenever this is possible, since there is virtually no resistance to breathing in the system. The spontaneous breathing of the patient 4 will then be apparent at the hand ventilator 40, however, the outlet valve 46 can be designed to be adjustable in order to achieve the greatest degree of patient safety. Pressure in the system can be regulated almost exactly according to measurements of system pressure by the pressure sensor 45.

As already noted, the anesthetic system 2 can also operate with other respiratory modes. For example, the switching valve 42 can be closed and the switching valve 26 can be set so the connection between the second gas reservoir 25 and the first gas reservoir 19 opens. Conventional mechanical ventilation of the patient can be performed in this I manner. An important difference, compared to previous closed, mechanical systems is that the control rod 20 and servo-motor 22 still control flow to and from the patient. This can be performed according to some appropriate reference value programmed by the physician. The reference value for the inspiration phase and expiration phase could e.g. be calculated from a desired tidal volume and inspiration time and expiration time respectively. A second flow meter, or pressure meter in this instance, is arranged in the line system to measure current values. For simplicity, these meters are not shown in FIGS. 1 and 2, since Swedish Published Application 470 417 clearly and exhaustively describe the way meters can be placed in an open line system in order to achieve the desired reference values. The corresponding meter locations are possible with all the system versions described in this application. Other options are to base the reference value on respiratory volume and/or estimated/measured $CO_2$ output and/or positive pressure in the system. These versions also apply to all the embodiments in this application.

Gas in the second gas reservoir 25 will be alternately transferred back and forth between the second reservoir 25 and the drive gas bellows 32 (which can be completely excluded in this position; one opening to ambient air is sufficient). Gas consumption can accordingly be kept to a minimal level, even during purely mechanical ventilation in a closed system. In this operating mode, the anesthetic system 2 is even able to operate in an emergency mode if power to or the anesthetic system 2 itself should fail. The drive gas bellows 32 can then be squeezed manually to compress, by transmission of pressure via a drive gas, the first bellows 18 and accordingly to force respiratory gas through the connecting line 10 and the inspiratory line 6 to the patient 4. Instead of manual compression in the latter operating mode, mechanical (motorized or pneumatic) compression of the drive gas bellows 32 can be used. In the latter instance, the anesthetic system 2 operates exactly as known closed systems (but with at least some of the above-noted advantages being retained), and an increased flow of fresh respiratory gas must be supplied via the ventilator unit 36, and the outlet valve 46 must be activated as an excess pressure valve (with the same function as a pop-off valve).

The anesthetic system 2 can also be set for other operating modes. For example, the outlet valve 46 can be opened completely, and control of the first bellows 18 can be blocked completely, an open system being achieved in which fresh gas is supplied to the patient 4 through the inspiratory line 6 from the ventilator unit 36 and expiration is via the expiratory line 8 straight to the evacuation line 48. All respiration is then completely controlled by the ventilator unit 36. If, in this situation, the user elects to connect the hand ventilator 40, by resetting the second switching valve 42, a function identical to that described in Swedish Published Application 470 417 becomes available. The open system is suitable when anesthetic is to be flushed out of the system.

The described anesthetic system 2 can therefore be set in a simple fashion for all kinds of operating modes, while still achieving highly accurate regulation of the supply of respiratory gas to the patient 4 in most of these modes. In particular, completely closed systems are achieved with a minimum of gas consumption. If the system, for any reason, needs a larger volume of gas exchange, the outlet valve 46, as already noted, can suitably be devised so it can be regulated. Pressures and flows at specific points in the system can then be sustained with a minimum of leakage. The anesthetic system 2 can also be devised so the switching between different operating modes is manual or automatic. One example of automatic switching is when the system is operating in the mechanical ventilation mode and the physician squeezes the hand ventilator 40. The system then automatically switches to manual ventilation. This is simply achieved by arranging a pressure meter in the hand ventilator 40. When the pressure increase in the hand ventilator 40 is big enough, the control unit sends a reswitching signal to the switching valves 26 and 42.

FIGS. 3 and 4 show a second embodiment of the anesthetic system according to the invention. The second embodiment is designated 50. The anesthetic system 50 is connected to a patient 52. The anesthetic system 50 has an inspiratory line 54, an expiratory line 56 and a connecting line 58. A first check valve 60, a second check valve 62 and a third check valve 64 are arranged in the connecting line 58 so that gas can only flow in one direction, i.e., from the expiratory line 56, through the connecting line 58 to the inspiratory line 54.

The connecting line 58 is connected to a bellows 66 whose interior space forms a first gas reservoir 67. As shown in FIG. 4, the bellows 66 can also be disconnected from the connection to the connecting line 58 by means of a first directional valve 68. The function and purpose of this will be apparent from the description below. The bellows 66 is located in a container 70, and the space between the bellows 66 and the outer wall of the container 70 can serve as a second gas reservoir 71 in certain operating positions for the anesthetic system 50. The second gas reservoir 71 is then connected to the connecting line 58 via a connection line 72. Like the bellows 66, the connection line 72 can be optionally connected to or disconnected from the second gas reservoir 71 via a second directional valve 74.

An anesthetic gas reflector 76 is arranged in the connection line 72. Its function will be apparent from the description below. An open connection to ambient air can be achieved, via an outlet valve 78, for the connection line 72. Fresh 35 respiratory gas can be supplied to the system through a fresh gas line 80 from a ventilator device 82. The ventilator device 82 contains inter alia a source of fresh gas and a control unit for controlling the entire anesthetic system 50. A hand ventilator 84 can be connected to the connecting line 58 and the inspiratory line 54 but, as in the previous embodiment, it can also be disconnected from the rest of the system by means of a third directional valve 86 (only shown in FIG. 4). In conjunction with the hand ventilator 84, a flow meter 88 is also arranged to measure the flow of gas to or from the hand ventilator 84, when the latter is connected to the line system.

As in the previous embodiment, a control rod 90 is mechanically connected to the bellows 66 to regulate the position of the bellows 66 and, accordingly, the volume inside (the first gas reservoir 67) and outside the bellows 66 (the second gas reservoir 71). The control rod 90 is rapidly and precisely regulated by a servo-motor 92. As FIGS. 3 and 4 show, the anesthetic system 50 also has a first outlet line 94 and a second outlet line 96 which can be respectively connected to the first and second gas reservoirs 67 and 71 in the bellows 66 and container 70 respectively.

FIG. 3 shows the anesthetic system 50 set up for manual ventilation with the hand ventilator 84. This is accomplished when the physician squeezes the hand ventilator 84, thereby forcing respiratory gas down through the inspiratory line 54 to the patient 52. At the same time, the servo-motor 92 regulates the control rod 90 so the bellows 66 is compressed at a rate equivalent to the flow of respiratory gas to the patient 52. The respiratory gas present inside the bellows is then forced into the connecting line 58 and on to the second check valve 62 in which gas is forced through the connection line 72 to the outlet valve 78 which is open in this situation, and respiratory gas is released into ambient air. Since the gas flows past the anesthetic gas reflector 76 during its passage, any anesthetic gas in the respiratory gas is adsorbed by the anesthetic gas reflector 76.

When the inspiratory phase ends and the physician releases his or her grip on the hand ventilator 84, expiration commences, and respiratory gas then flows from the patient 52, through the expiratory line 56 to the connecting line 58. Respiratory gas then passes the first check valve 60 and is drawn into the bellows 66 which, at this stage, is regulated by the control rod 90 and servo-motor 92 so the volume in the first gas reservoir 67 increases at a rate corresponding to hand ventilator flow and, accordingly, the patient's expiratory flow. At the same time as the bellows 66 fills with expired respiratory gas from the patient 52, fresh breathing (with or without a fraction of the desired concentration of anesthetic gas) is supplied from the ventilator unit 82, via the fresh gas line 80 and the connection line 72 to the connecting line 58. Respiratory gas continues on to the anesthetic gas reflector 76 in the opposite direction, and anesthetic gas previously adsorbed by the reflector 76 is then desorbed and picked up by the respiratory gas. This new respiratory gas then passes the third check valve 64 to fill the hand ventilator 84. This takes place with exactly the same flow as the flow exhaled by the patient 52, and the physician will not notice any difference compared to the situation in which the patient 52 exhales straight into the hand ventilator 84. Throughout the breathing cycle, the second gas reservoir 71 is openly connected to ambient air via the outlet line 94, so air will be drawn into or forced out of the line respectively, depending on whether the breathing cycle is in an inspiratory phase or an expiratory phase. The concentration of anesthetic can be checked with an appropriately situated anesthetic gas analyzer (not shown in FIGS. 3 and 4).

FIG. 4 shows a second operating mode for the anesthetic system 50. At this stage, the first directional valve 68 is set so the first gas reservoir 67 is instead in direct connection with ambient air via the second outlet line 96, the second directional valve 74 having been placed so the second gas reservoir 71 is in direct connection with the connection line 72 and the third directional valve 86 having closed the connection between the connecting line 58 and the hand ventilator 84. This operating mode corresponds to mechanical ventilation. In the same way as in mechanical ventilation with the first embodiment, a reference value is set for flow or pressure, and the current measurement value is measured by meters (not shown).

During inspiration in this operating mode, fresh respiratory gas flows out of the ventilator unit 82, through the fresh gas line 80 and anesthetic gas reflector 76, to the inspiratory line 54 and the patient 52. Here, anesthetic gas in the anesthetic gas reflector 76 is picked up by the respiratory gas before the respiratory gas passes through the connecting line 58, the third check valve 64 and the inspiratory line 54 to the patient 52. At the same time as this gas flows to the patient 52, the servo-motor 92 regulates the control rod 90 so that the bellows 66 expands and forces gas out of the second gas reservoir 71 to the connection line 72 and the output valve 78, which is open to ambient air during inspiration.

When expiration is to start, the outlet valve 78 closes, and the servo-motor 92 regulates the control rod 90 so the bellows 66 compresses at a rate causing the increase in the volume of the second reservoir 71 to correspond to the flow of respiratory gas from the patient 52. Here, the bellows 66 opposes the resistance to flow which is caused by the check valves 60, 62 and 64 and the anesthetic gas reflector 76 in the first embodiment. Expired respiratory gas thus flows through the expiratory line 56, the connecting line 58 (with the first check valve 60 and the second check valve 62), the anesthetic gas reflector 76 and on to the second gas reservoir 71 via the connector line 72. When expiration 5 concludes, the next inspiration phase commences in the manner already described.

Since no carbon dioxide absorber is required in the second embodiment, sevoflurane can be used to advantage in a completely closed system with the anesthetic system 50.

When the directional valves 68, 74 and 86 are regulated in an appropriate manner during the respiratory cycle, the anesthetic system 50 can also operate in other operating modes. These modes are of limited interest, however, since the anesthetic gas reflector 76 conveys the system's biggest advantages when employed in one of the ways described above.

In most of the above-described embodiments, at least one gas reservoir functions as a storage location or an intermediate storage location in the anesthetic system. In the latter instance (FIG. 3 and, in particular, FIG. 4), almost all respiratory gas in the gas reservoir is discharged into ambient air and is not sent to the patient or hand ventilator. In the first embodiment, both gas reservoirs serve as temporary gas storage locations, before the hand ventilator fills with respiratory gas. The mechanically controlled bellows thus has a fundamentally different function in most of the embodiments than a bellows in prior art anesthetic systems. The bellows is only used in one embodiment (FIGS. 1 and 2 set up for mechanical ventilation) for regulating the patient's breathing.

The check valves can be replaced with fans or other devices capable of regulating the direction of gas flow.

Anesthetic agents can be introduced anywhere in the circular system, i.e. into fresh gas from the ventilator, into the inspiratory line, into the expiratory line or into the connecting line. Anesthetic can be introduced in the gaseous or liquid state. An anesthetic analyzer can be installed anywhere in the circular system, i.e. in the inspiratory line, the expiratory line or the connecting line, for monitoring and/or controlling the system's concentration of anesthetic gas. One or more redundant anesthetic gas sensors can be connected to increase safety and/or reliability.

Figure 5:
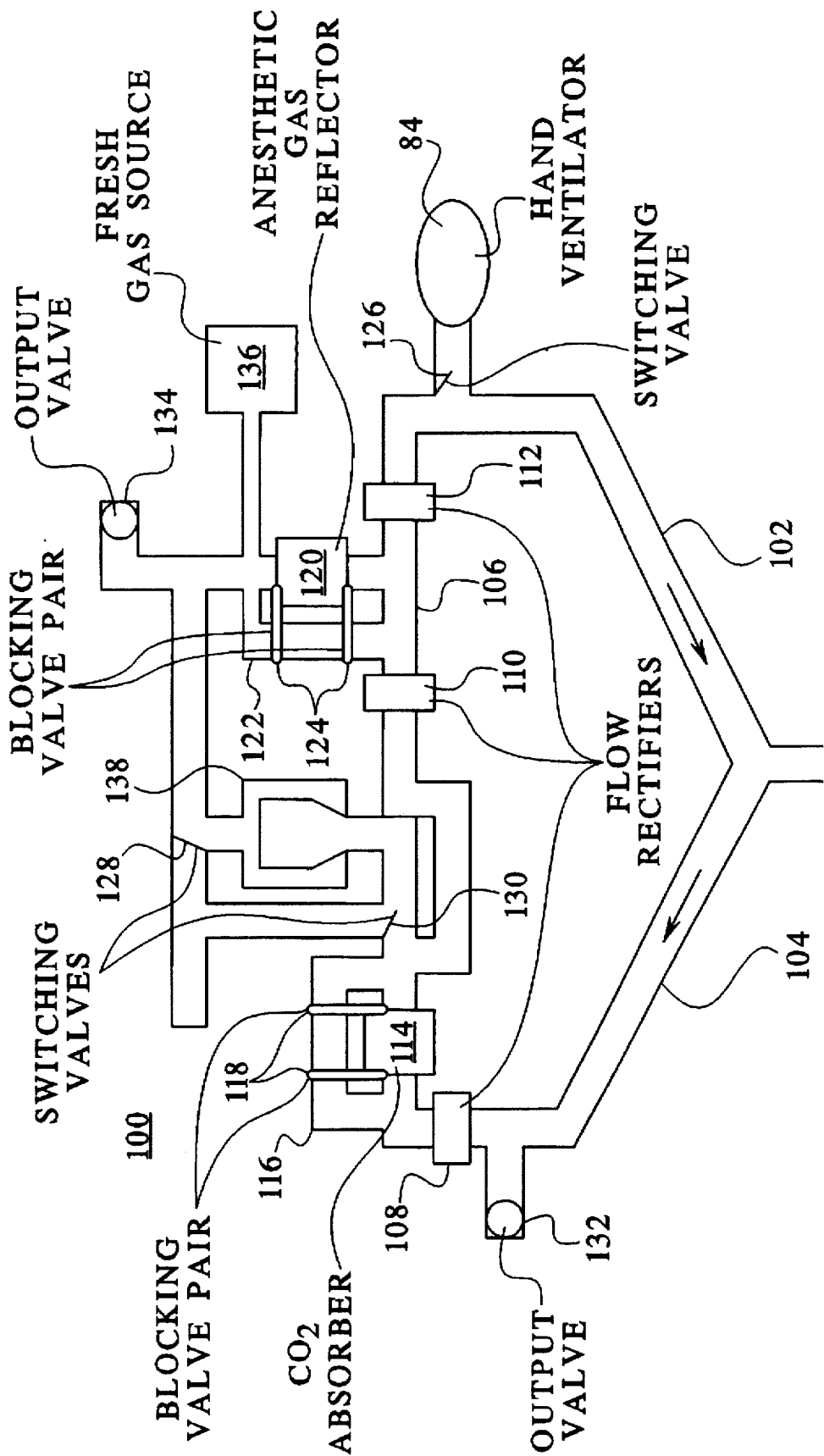
FIG. 5 is a schematic illustration of a third embodiment of the anesthetic system according to the invention.

Various detailed configurations stated in the above embodiments can be combined and switched between embodiments. The anesthetic system can also be devised so that switching between systems with an absorber and systems with a reflector is easily performed, e.g. with the aid of quick couplings, to permit the replacement of requisite components. FIG. 5 illustrates the principles for an anesthetic system 100 in which minimum replacement of components is necessary for switching to systems with an absorber and systems with a reflector and vice-versa. FIG. 5 only shows the components of relevance to component replacement.

The anesthetic system 100 has an inspiratory line 102, an expiratory line 104 and a connecting line 106. Three flow rectifiers 108, 110 and 112 are arranged in the connecting line 106. The flow rectifiers 108, 110 and 112 can be fans which control the direction of respiratory gas flow through the lines 102, 104 and 106 but can alternatively be check valves or the equivalent. Combinations of different kinds of flow rectifiers 108, 110 and 112 is also feasible. The flow rectifiers 108, 110, 112 can be suitably activated so that they only control the direction of flow when activated. When they are not activated, they do not impede gas flow in any direction. In this manner, the flow rectifiers 108, 110 and 112 required in each type of special set-up of the anesthetic system 100 can be enabled when needed.

A $CO_2$ absorber 114 can be connected to the connecting line 106 with a quick coupling. A first bypass line 116 runs parallel to the $CO_2$ absorber 114. The first bypass line 116 is closed off by a first blocking valve pair 118 when the $CO_2$ absorber 114 is connected. When no $CO_2$ absorber 114 is connected, the first bypass line 116 is open to gas flows, and the first blocking valve pair 118 prevent gas from leaking out at the $CO_2$ absorber's 114 connector part.

In the corresponding manner, an anesthetic gas reflector 120 can be hooked up to the anesthetic system 100 by means of a quick coupling. A second bypass line 122 and a second blocking valve pair 124 have the same purpose as the first bypass line 116 and the first blocking valve pair 118.

The quick connectors also make possible fast and safe replacement of the $CO_2$ absorber 114 or anesthetic gas reflector 120 during operation.

The anesthetic system 100 also has a first switching valve 126 for connecting and disconnecting the hand ventilator 84, a second switching valve 128 for switching between manual and mechanical ventilation and a third switching valve 130 for switching between manual and mechanical ventilation when an anesthetic gas reflector 120 is installed.

There is also a first output valve 132, a second output valve 134, a source of fresh gas 136 and a bellows system 138. The function of these and operating modes possible with the anesthetic system 100 are apparent from the previous embodiments.

Although modifications and changes may be suggested by those skilled in the art, it is the intention of the inventor to embody within the patent warranted hereon all changes and modifications as reasonably and properly come within the scope of his contribution to the art.

I claim as my invention:

1. An anesthetic administration system comprising:

an inspiration line connectable to a patient for delivering a respiratory gas to said patient;

an expiratory line connectable to said patient for carrying expired respiratory gas from said patient;

a gas reservoir connected to said inspiration line and to said expiration line, said gas reservoir having a variable volume which, during a respiration cycle of said patient, is alternately filled and emptied of respiratory gas; and control means, connected to said gas reservoir, for actively regulating the volume of said gas reservoir relative to a reference value throughout a breathing cycle of said patient.

2. An anesthetic administration system as claimed in claim 1 further comprising: a connecting line interconnecting said inspiration line and said expiration line;

first means, disposed in said connecting line next to and upstream from said gas reservoir, for controlling a direction of flow of said respiratory gas;

second means, disposed in said connecting line next to and downstream from said gas reservoir, for controlling a direction of flow of said respiratory gas; and a fresh gas source being in communication with said inspiratory line downstream from said second means.

3. An anesthetic administration system as claimed in claim 2 wherein said fresh gas source is connected to said inspiratory line.

4. An anesthetic administration system as claimed in claim 2 wherein said fresh gas source is connected to said connecting line.

5. An anesthetic administration system as claimed in claim 2 wherein said patient consumes a first amount of gas during said breathing cycle, and said system further comprising:

a carbon dioxide filter disposed in said connecting line, upstream from said gas reservoir, for absorbing carbon dioxide in said expired respiratory gas, said carbon dioxide filter absorbing a second amount of gas; and said control means comprising means for regulating said fresh gas source for supplying a total amount of fresh gas to said system corresponding to said first and second amounts and any leakage.

6. An anesthetic administration system as claimed in claim 2 further comprising:

manual ventilator means, connected to said inspiratory line downstream from said fresh gas source, for, when operated, causing respiratory gas to flow from said manual ventilator means through said inspiration line to said patient during inspiration;

a flow meter disposed in said inspiration line for measuring a flow of said respiratory gas from said manual ventilator means to obtain a measured flow, said measured flow comprising said reference value for said control means;

said gas reservoir comprising a bellows;

a hermetically sealed container in which said bellows is disposed, said container having a predetermined volume and a space between said bellows and said container forming a further gas reservoir, said container being connected to said connecting line downstream from said second means; and said control means comprising means for regulating the volume of said bellows for causing respiratory gas to flow from an interior of said bellows to said further gas reservoir during inspiration, and from said further gas reservoir to said manual ventilator means and from said patient to said interior of said bellows during expiration.

7. An anesthetic administration system as claimed in claim 2 further comprising:

an anesthetic gas reflector connected between said fresh gas source and said connecting line;

third means for controlling the flow of respiratory gas disposed in said connecting line downstream from said anesthetic gas reflector;

a gas release having an outlet valve, controlled by said control means, connected to said gas reservoir; and said control means comprising means for opening said outlet valve during inspiration for permitting said gas reservoir to release expired respiratory gas via said outlet valve and for regulating said outlet valve during expiration for permitting said gas reservoir to release a volume of gas, corresponding to a volume exiting said gas reservoir and then closing said outlet valve for permitting said gas reservoir to fill with expired respiratory gas.

8. An anesthetic administration system as claimed in claim 7 wherein said gas reservoir and said gas outlet are connected to said connecting line through said anesthetic gas reflector, with expired respiratory gas being carried from said patient to said gas reservoir through said anesthetic gas reflector during expiration, and fresh gas being supplied from said fresh gas source to said patient through said anesthetic gas reflector during inspiration.

9. An anesthetic administration system as claimed in claim 7 further comprising:

manual ventilator means connected to said inspiratory line for causing respiratory gas to flow from said hand ventilator means through said inspiratory line to said patient during inspiration;

a flow meter disposed to measure a flow of said respiratory gas from said hand ventilator means to obtain a measured flow, said measured flow comprising said reference value for said control means; and said gas outlet being connected to said connecting line through said anesthetic gas reflector so that expired respiratory gas is carried from said gas reservoir to said gas outlet through said anesthetic gas reflector during inspiration, and fresh respiratory gas is carried from said fresh gas source to said hand ventilator means during expiration.

10. An anesthetic administration system as claimed in claim 7 wherein said third means comprises a one-way valve.

11. An anesthetic administration system as claimed in claim 7 wherein said third means comprises a fan.

12. An anesthetic administration system as claimed in claim 2 wherein said first and second means each comprise a one-way valve.

13. An anesthetic administration system as claimed in claim 2 wherein said first and second means each comprise a fan.

14. An anesthetic administration system as claimed in claim 1 further comprising means for obtaining a measured value of at least one parameter selected from the group of respiratory gas flow, respiratory gas pressure, respiratory volume and $CO_2$ production by said patient, said measured value comprising said reference value.

* * * * *